United States Patent
Haidukewych et al.

(10) Patent No.: US 9,295,504 B2
(45) Date of Patent: Mar. 29, 2016

(54) INTRAMEDULLARY NAIL WITH LOCKING KEY

(75) Inventors: George J. Haidukewych, Tampa, FL (US); Daniel S. Horwitz, Salt Lake City, UT (US); Frank A. Liporace, Fort Lee, NJ (US); Andrew Sems, Oronoco, MN (US); Peter Giannoudis, Leeds (GB) (US); Anthony J. Metzinger, Winona Lake, IN (US); Charles D. Christie, Warsaw, IN (US); Andrew H. Berthusen, Warsaw, IN (US)

(73) Assignee: Biomet C.V., Gibraltar ( * ) Notice: Subject to any disclaimer, the term of this patent is extended or adjusted under 35 U.S.C. 154(b) by 703 days.

(21) Appl. No.: 12/415,212

(22) Filed: Mar. 31, 2009

(65) Prior Publication Data
US 2010/0249781 A1    Sep. 30, 2010

(51) Int. Cl.
*A61B 17/72*    (2006.01)
*F16B 39/28*    (2006.01)
F16B 39/06    (2006.01)

(52) U.S. Cl.
CPC ........... *A61B 17/7241* (2013.01); *A61B 17/725* (2013.01); *F16B 39/06* (2013.01)

(58) Field of Classification Search
CPC .............. A61B 17/72; A61B 17/7233; A61B 17/7241; A61B 17/68; F16B 39/284; F16B 39/34; F16B 33/002
USPC ...................................... 606/62–68
See application file for complete search history.

(56) References Cited

U.S. PATENT DOCUMENTS

| 929,084 | A | * | 7/1909 | George | 411/292 |
| 2,377,186 | A | * | 5/1945 | Rohmer | 411/293 |
| 2,855,970 | A | * | 10/1958 | Neuschotz | 411/110 |

(Continued)

FOREIGN PATENT DOCUMENTS

| EP | 0257118 A1 | 3/1988 |
| EP | 0586824 A1 | 3/1994 |

(Continued)

OTHER PUBLICATIONS

International Search Report in corresponding PCT application (i.e., PCT/US2010/028816), mailed Jul. 20, 2010 (4 pages).

(Continued)

*Primary Examiner* — Eduardo C Robert
*Assistant Examiner* — Jacqueline Johanas
(74) *Attorney, Agent, or Firm* — Schwegman Lundberg & Woessner, P.A.

(57) ABSTRACT

An intramedullary nail comprises longitudinal channel, a first transverse passage and a second transverse passage. A lag screw extends through the first transverse passage of the intramedullary nail. An anti-rotation shaft extends through the second transverse passage of the intramedullary nail. A cannulated lag screw lock is positioned in the intramedullary shaft and engages the lag screw. The anti-rotation shaft extends through a cross channel in the lag screw lock. A second shaft lock is positioned in the intramedullary nail with the second shaft lock engaging the anti-rotation shaft. In at least one embodiment, the lag screw lock includes a substantially cylindrical body portion rotatably connected to a threaded head portion. In at least one embodiment, the second shaft lock is provided as an end cap including a threaded upper portion and a lower post portion that extends into the lag screw lock.

5 Claims, 5 Drawing Sheets

(56) References Cited

U.S. PATENT DOCUMENTS

| | | | |
|---|---|---|---|
| 3,103,962 A * | 9/1963 | Neuschotz | 411/110 |
| 3,667,526 A * | 6/1972 | Neuschotz | 411/110 |
| 3,908,727 A * | 9/1975 | Osborne | 411/304 |
| 4,776,330 A | 10/1988 | Chapman et al. | |
| 4,895,485 A * | 1/1990 | Guevara et al. | 411/322 |
| 5,028,191 A * | 7/1991 | Rowley et al. | 411/292 |
| 5,176,681 A | 1/1993 | Lawes et al. | |
| 5,263,955 A | 11/1993 | Baumgart et al. | |
| 5,411,357 A * | 5/1995 | Viscio et al. | 411/110 |
| 5,454,813 A | 10/1995 | Lawes | |
| 5,573,536 A | 11/1996 | Grosse et al. | |
| 5,766,174 A | 6/1998 | Perry | |
| 5,968,047 A * | 10/1999 | Reed | 606/76 |
| 6,123,708 A | 9/2000 | Kilpela et al. | |
| 6,168,595 B1 | 1/2001 | Durham et al. | |
| 6,221,074 B1 | 4/2001 | Cole et al. | |
| 6,228,086 B1 | 5/2001 | Wahl et al. | |
| 6,235,031 B1 | 5/2001 | Hodgeman et al. | |
| 6,406,477 B1 | 6/2002 | Fujiwara | |
| 6,409,730 B1 * | 6/2002 | Green et al. | 606/232 |
| 6,562,042 B2 | 5/2003 | Nelson | |
| 6,579,294 B2 | 6/2003 | Robioneck | |
| 6,582,453 B1 * | 6/2003 | Tran et al. | 606/232 |
| 6,648,889 B2 | 11/2003 | Bramlet et al. | |
| 6,652,528 B2 | 11/2003 | Vandewalle | |
| 6,835,197 B2 | 12/2004 | Roth et al. | |
| 6,932,819 B2 | 8/2005 | Wahl et al. | |
| 7,306,600 B2 | 12/2007 | Roth et al. | |
| 7,601,153 B2 * | 10/2009 | Shinjo et al. | 606/64 |
| 7,763,022 B2 | 7/2010 | Speitling et al. | |
| 7,883,529 B2 * | 2/2011 | Sinnott et al. | 606/232 |
| 8,029,478 B2 * | 10/2011 | Zanella | 604/175 |
| 8,092,454 B2 | 1/2012 | Sohngen | |
| 8,454,606 B2 | 6/2013 | Frigg et al. | |
| 8,702,707 B2 | 4/2014 | Sohngen | |
| 2001/0012939 A1 | 8/2001 | Wahl et al. | |
| 2001/0034523 A1 | 10/2001 | Nelson | |
| 2002/0032445 A1 * | 3/2002 | Fujiwara | 606/67 |
| 2002/0156473 A1 | 10/2002 | Bramlet et al. | |
| 2003/0004514 A1 * | 1/2003 | Frigg et al. | 606/62 |
| 2003/0018336 A1 | 1/2003 | Vandewalle | |
| 2003/0074000 A1 | 4/2003 | Roth et al. | |
| 2003/0171819 A1 | 9/2003 | Sotereanos | |
| 2003/0195515 A1 | 10/2003 | Sohngen | |
| 2004/0230196 A1 * | 11/2004 | Martello | 606/73 |
| 2005/0069397 A1 * | 3/2005 | Shavit et al. | 411/457 |
| 2005/0090821 A1 | 4/2005 | Berrevoets et al. | |
| 2005/0143739 A1 * | 6/2005 | Shinjo et al. | 606/62 |
| 2005/0203510 A1 * | 9/2005 | Sohngen | 606/60 |
| 2006/0106389 A1 * | 5/2006 | Reber et al. | 606/72 |
| 2008/0119895 A1 * | 5/2008 | Manceau | 606/280 |
| 2008/0183171 A1 * | 7/2008 | Elghazaly et al. | 606/64 |
| 2008/0221577 A1 * | 9/2008 | Elghazaly | 606/64 |
| 2008/0294164 A1 * | 11/2008 | Frank et al. | 606/64 |
| 2012/0076578 A1 * | 3/2012 | Schron et al. | 403/376 |
| 2012/0157997 A1 | 6/2012 | Sohngen | |

FOREIGN PATENT DOCUMENTS

| | | |
|---|---|---|
| EP | 0727189 A1 | 8/1996 |
| EP | 0838199 A1 | 4/1998 |
| EP | 1175872 A2 | 1/2002 |
| EP | 1175872 A3 | 11/2003 |
| JP | 02021859 A | 1/1990 |
| JP | 11137566 A | 5/1999 |
| JP | 2000342596 A | 12/2000 |
| JP | 2003533242 A | 11/2003 |
| JP | 2002035000 A | 2/2005 |
| JP | 2005205201 A | 8/2005 |
| WO | 0076414 A1 | 12/2000 |
| WO | 0143652 A1 | 6/2001 |
| WO | 01054598 A1 | 8/2001 |
| WO | 02067794 A1 | 9/2002 |
| WO | WO-02098330 A2 | 12/2002 |
| WO | 03061495 A2 | 7/2003 |
| WO | WO-03094763 A1 | 11/2003 |
| WO | WO-2004002342 A2 | 1/2004 |
| WO | 2009002890 | 12/2008 |

OTHER PUBLICATIONS

"International Application Serial No. PCT/US2010/028816, International Search Report mailed Jul. 20, 2010", 4 pgs.

* cited by examiner

INTRAMEDULLARY NAIL WITH LOCKING KEY

TECHNICAL FIELD

The present invention relates generally to the field of orthopaedic trauma, and more particularly to a device for positioning in the medullary canal of a long bone.

BACKGROUND

The skeletal system includes many long bones that extend from the human torso. These long bones include the femur, fibula, tibia, humerus, radius and ulna. These long bones are particularly exposed to trauma from accidents, and, as such, may be easily fractured.

When a fracture occurs, the distal end or proximal portions of the long bone may be fractured into several components and must be realigned. For example, subtrochanteric and femoral shaft fractures of femurs are often accompanied by fractures of the femoral neck portion and head portion. Areas around the greater trochanter and lesser trochanter may also fracture.

Mechanical devices, commonly in the forms of pins, plates, screws, nails, wires and external devices are commonly used to attach fractured long bones. The pins, plates, wires, nails and screws are typically made of a durable material compatible to the human body, for example titanium, stainless steel or cobalt chromium.

One mechanical device commonly used to treat subtrochanteric and femoral shaft fractures is the intramedullary rod or nail. The intramedullary nail is typically provided as a cannulated shaft that is inserted into the marrow canal of the femur or other long bone in order to stabilize the fractured bone parts. Before the intramedullary nail is inserted into a long bone, a ball-nose guide wire is typically inserted into the bone canal. The intramedullary nail follows the guide wire into the canal. The guide wire is then removed from the canal and further work may be done on the bone with the implanted intramedullary nail.

Intramedullary rods or nails are often provided with openings for receiving transverse screws or pins. These transverse screws are used to secure the femoral bone fragments, for example the greater trochanter, the lesser trochanter, the neck portion, and the head portion. When securing bone fragments of the neck portion and head portion of the femur, a transverse screw in the form of a lag screw is typically fitted through an opening in the intramedullary nail and screwed into the neck portion and head portion of the fractured femur. At the option of the surgeon, an anti-rotation peg or screw may also be positioned in a second opening in the intramedullary nail to provide a more rigid construction for securing the fractured bone fragments of the femoral neck and head.

To promote the healing of the bone fracture the lag screw and anti-rotation screw are designed to provide a load or force on the reduction or fracture site. Accordingly, the lag screw and anti-rotation screw are designed to provide for sliding compression or movement of the screws in the openings of the intramedullary nail when the intramedullary nail is implanted in the patient during surgery. However, following implantation, during the healing process, movement of the screws relative to the bone is undesirable.

In order to reduce movement of the screws following surgery, some locking device is typically inserted into the intramedullary nail to engage the screws and limit their motion relative to the nail. However, before the locking piece may be inserted into the nail, the ball-nose guide wire must first be removed from the nail. Thus, the locking device is not typically preinstalled in the intramedullary nail and instead must be inserted during the surgical procedure. This process of installing the locking device takes up valuable time during the surgery and is generally inconvenient for the surgeon. Accordingly, it would be advantageous to provide an intramedullary nail arrangement having a locking piece that is pre-installed in the nail before the surgical procedure.

During a surgical procedure where the surgeon uses both a lag screw and an anti-rotation screw, a surgeon may wish to independently lock down the lag screw or the anti-rotational screw to control the rotational and axial translation of one screw while allowing the other screw to move independently. However, current intramedullary nail arrangements do not provide the option to lock down the lag screw while allowing the anti-rotation screw to move independently. Accordingly, it would also be advantageous to provide an intramedullary nail arrangement where the lag screw may be locked down while still allowing the anti-rotation screw to move independently.

Some prior art arrangements have utilized a set screw and spacer provided in the intramedullary nail to control the lag screw. However, in these arrangements, the set screw and spacer are two separate pieces. This is also not optimal because the complete assembly is not cannulated and does not allow the lag screw to translate along its axis. Furthermore, other proposed arrangements for controlling movement of the lag screw do not allow for an anti-rotation screw when desired. For these intramedullary nails having a lag screw but no option for an anti-rotation screw, some means may be provided to screw down a pin or rod to either statically lock the lag screw or only allow translation. However, in past arrangements calling for both a lag screw and an anti-rotation screw no means is provided for controlling only the lag screw with the anti-rotation screw in place or for locking the lag screw while still allowing translation of the anti-rotation screw.

Therefore, it would be advantageous to provide an improved intramedullary nail assembly. As discussed above, it would be particularly advantageous to provide an intramedullary nail assembly where a locking piece may be preinstalled in the nail prior to surgery. It would also be advantageous if such intramedullary nail assembly was configured to include both a lag screw and an optional anti-rotation screw that may be selectively locked in place on the nail assembly. Furthermore, it would be advantageous if the intramedullary nail assembly included an arrangement to control movement of the lag screw with the anti-rotation screw in place in the intramedullary nail or for locking only the lag screw while still allowing translation of the anti-rotation screw within the intramedullary nail.

SUMMARY

According to one embodiment of the present disclosure, an intramedullary nail comprises longitudinal channel, a first transverse passage and a second transverse passage. A lag screw extends through the first transverse passage of the intramedullary nail. An anti-rotation shaft extends through the second transverse passage of the intramedullary nail. A cannulated lag screw lock is positioned in the intramedullary shaft and engages the lag screw. The anti-rotation shaft extends through a cross channel in the lag screw lock. A second shaft lock is positioned in the intramedullary nail with the second shaft lock engaging the anti-rotation shaft.

In at least one embodiment, the lag screw lock includes a substantially cylindrical body portion rotatably connected to a threaded head portion. The threaded head portion includes threads that engage complimentary threads on an interior portion of the intramedullary nail. Accordingly, rotation of the threaded head portion results in movement of the cylindrical body portion along a longitudinal axis of the intramedullary nail. The lag screw lock is substantially cylindrical in form and cannulated with a longitudinal passage that is aligned with and opens to the longitudinal channel of the intramedullary nail. The cross channel extends through the main body portion such that the anti-rotation shaft passes through the main body portion of the lag screw lock member when the anti-rotation shaft is inserted into the intramedullary nail.

In at least one embodiment, the second shaft lock is provided as an end cap positioned in the longitudinal channel of the intramedullary nail. The impinging end cap includes a threaded upper portion and a lower post portion. The threaded upper portion includes threads configured to engage the complimentary threads in the longitudinal channel of the intramedullary nail. The post portion includes a locking surface configured to extend into the longitudinal passage of the lag screw lock and engage the anti-rotation shaft to lock the anti-rotation shaft in place relative to the intramedullary nail.

The cannulation of the intramedullary nail and lag screw lock allows the nail and lag screw lock to be inserted over a ball nose guidewire. Having the lag screw lock preinstalled in the intramedullary nail decreases surgery time by only requiring a small adjustment to the lag screw lock in order to lock the lag screw in place.

Although various embodiments are disclosed herein, it will be appreciated by those of skill in the art that other implementations and adaptations are possible. Furthermore, aspects of the various embodiments described herein may be combined or substituted with aspects from other features to arrive at different embodiments from those described herein. Thus, it will be appreciated that various of the disclosed embodiments and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

DETAILED DESCRIPTION

Figure 1:
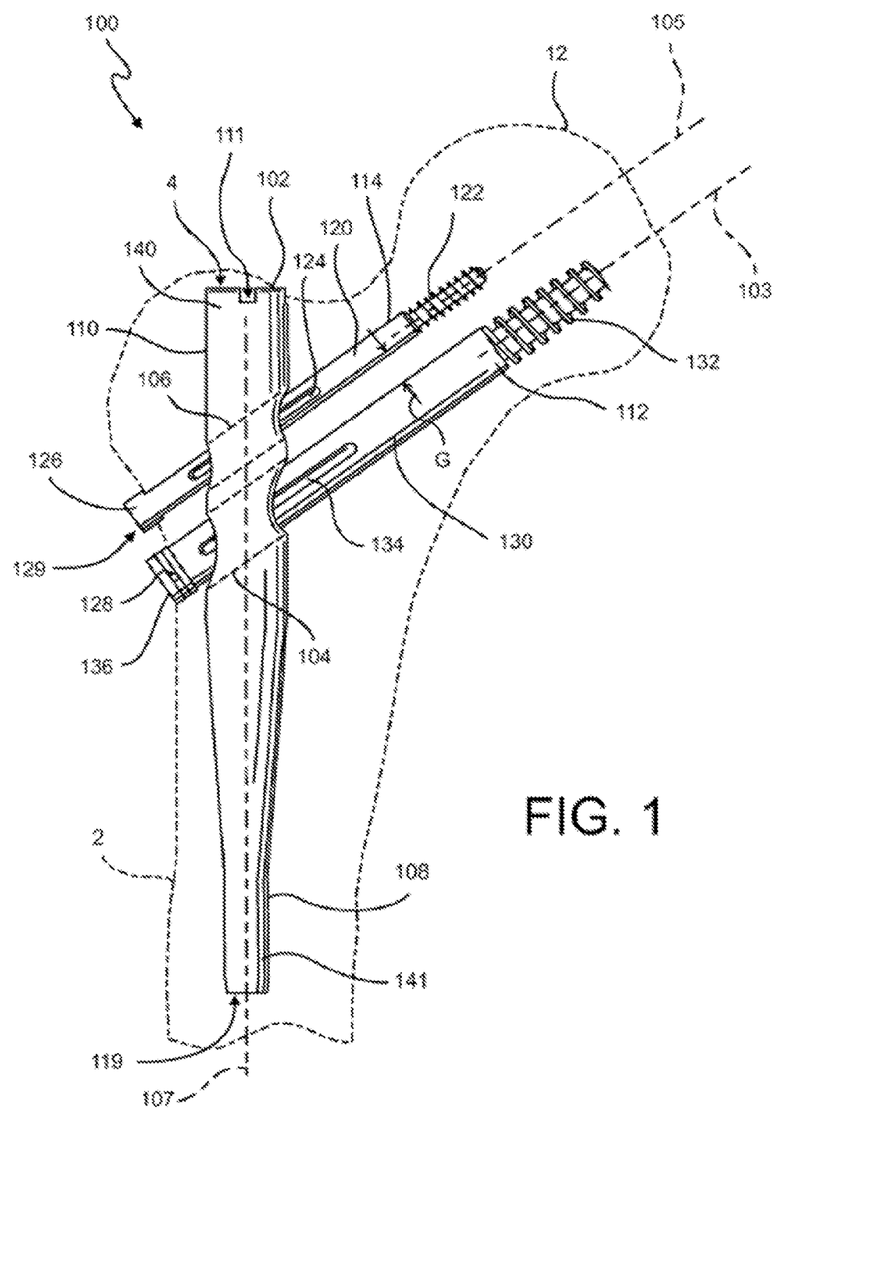
FIG. 1 is an anterior-posterior view of an embodiment of an intramedullary nail assembly with locking key assembly implanted in a femur.

Referring now to FIG. 1 a nail assembly 100 is shown for use in trauma surgery. The nail assembly 100 is designed for use in a long bone, such as a femur 2. The nail assembly 100 includes a generally hollow intramedullary shaft 102. In the embodiment of FIG. 1, the intramedullary shaft 102 is provided as an intramedullary nail. The intramedullary shaft 102 is elongated and defines a longitudinal shaft axis 107. The intramedullary shaft 102 includes a first transverse passage 104 (shown in dotted lines in FIG. 1) that extends completely through the intramedullary shaft 102. The first transverse passage is designed and dimensioned to receive a lag screw 112 in a slideable relationship with the intramedullary shaft 102. The intramedullary shaft 102 also includes a second transverse passage 106 (shown in dotted lines in FIG. 1) that extends completely through the intramedullary shaft 102. The second transverse passage 106 is designed and dimensioned to receive an anti-rotation member 114 in a slideable relationship with the intramedullary shaft 102. The first transverse passage 104 and the second transverse passage 106 are arranged parallel to each other, with the axis 103, 105 of each passage 104, 106 intersecting the shaft axis 107.

The intramedullary shaft 102 is designed and dimensioned to be fitted into a long bone, such as the medullary canal 4 of the femur 2, as shown in the embodiment of FIG. 1. In this case, since the medullary canal 4 is generally cylindrical, the intramedullary shaft 102 also has a generally cylindrical shape. The intramedullary shaft 102 includes a distal portion 108 having a smaller diameter than a proximal portion 110 of the intramedullary shaft 102. The shaft 102 is elongated with a length greater than its width or diameter and is designed to extend partially or substantially the entire length of the intramedullary canal 4 of the femur 2. The intramedullary shaft 102 may be straight or may be slightly arcuate to conform to the natural arc of the femur 2. The shaft 102 is generally cannulated with a mouth or opening 111 in an upper portion 140 of the shaft 102 that leads to a longitudinal channel 109 (not shown in FIG. 1; see FIGS. 3 and 4). An opening 119 is also provided at the bottom portion 141 of the shaft 102 and provides access to the longitudinal channel 109.

Figure 7:
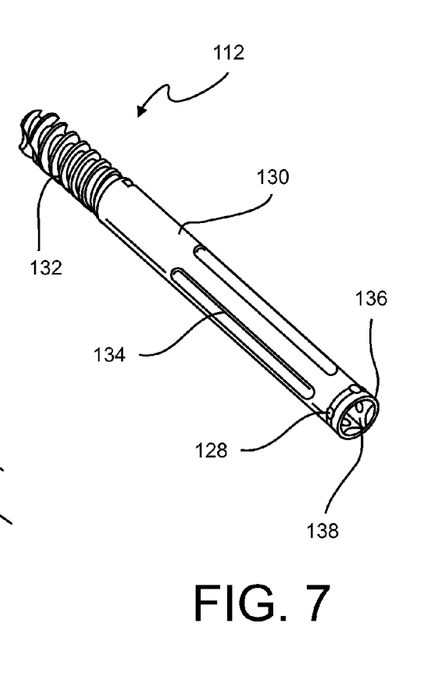
FIG. 7 shows a perspective view of a lag screw of the intramedullary nail assembly of FIG. 1.

The first transverse passage 104 of the nail 102 is configured to receive the lag screw 112. As shown in FIG. 1, when the nail assembly 100 is assembled, the lag screw 112 extends completely through the first transverse passage 104 and is slideably positioned within the passage 104 along axis 103. As can be seen in both FIG. 1 and FIG. 7, the lag screw 112 includes a generally cylindrical stem 130 with distal threads 132 extending from an end of the stem 130. A plurality of longitudinal grooves 134 extend along the stem 130. The grooves 134 are evenly spaced every ninety degrees on the outer surface of the stem 130. A head 136 of the lag screw includes a slot 138 (see FIG. 3) that serves as drive surface for the lag screw 112. The head 136 of the lag screw 112 also includes suture holes 128. The suture holes 128 provide the surgeon with the option of further securing the fracture to the lag screw 112 using sutures that pass through the suture holes 128.

The second transverse passage 106 of the nail 102 is configured to receive an anti-rotation member 114. As shown in FIG. 1, when the nail assembly 100 is assembled to include the anti-rotation member 114, the anti-rotation member 114 extends completely through the second transverse passage 106 and is slideably positioned within the passage 106 along axis 105. In the embodiment of FIG. 1, the anti-rotation member 114 is provided as an elongated shaft or screw. As shown in FIG. 1, the anti-rotation screw 114 includes a generally cylindrical stem portion 120 with distal threads 122 provided on an end of the screw. A plurality of longitudinal grooves 124 extend along the stem portion 120. The grooves 124 are evenly spaced every ninety degrees on the outer surface of the stem 120. A proximal head 126 of the anti-rotation screw 114 includes a slot 129 (see FIG. 3) that serves as drive surface.

With continued reference to FIG. 1, the lag screw 112 is spaced a distance G from anti-rotation screw 114 when the assembly is implanted in a patient. The distance G is sufficient to stabilize the head 12 of the femur 2 when the lag screw 112 and the anti-rotation screw 114 are engaged with a fractured head 12. Because the anti-rotation screw 114 is capable of sliding within the second transverse passage 106 and because the lag screw 112 is capable of sliding within the first transverse passage 104, the arrangement 100 provides for sliding compression of the fracture and promotes the healing process.

Although the lag screw 112 and anti-rotation screw 114 have been described herein as screws, it will be recognized that these shaft members may also be provided in various alternative embodiments, such as a nail, pin or other shaft member. Furthermore, in various embodiments, one of the shaft members may be a screw and the other shaft member may be a pin or non-threaded shaft member. However, in the embodiment of FIG. 1, the lag screw 112 and anti-rotation member 114 are both provided in the form of bone screws with each screw including a stem as well as threads extending from an end of the stem.

Figure 2:
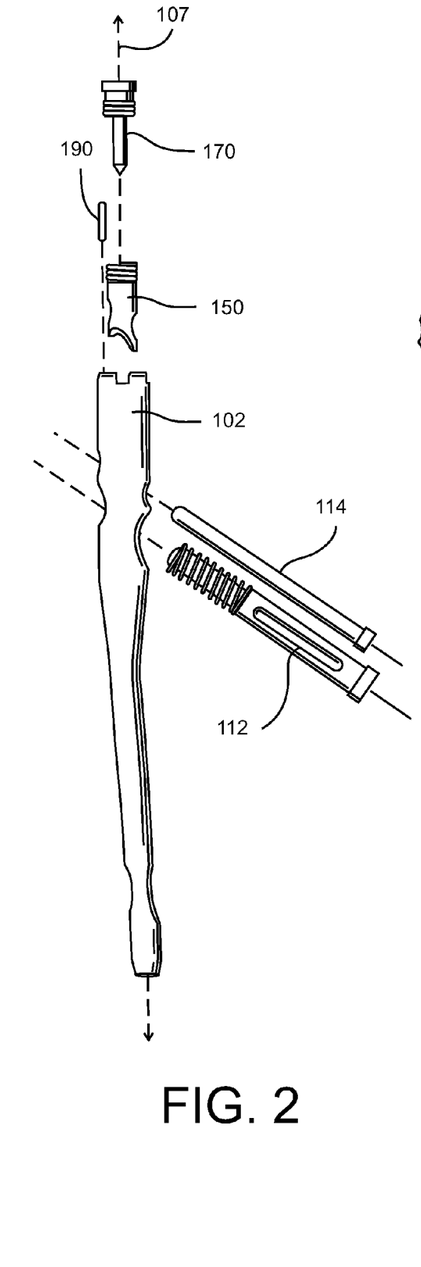
FIG. 2 is an exploded reverse side view of the intramedullary nail assembly of FIG. 1.

FIG. 2, shows an exploded view of the intramedullary nail assembly 100 of FIG. 1 with the internal components of the assembly removed from the intramedullary shaft 102 along axis 107. As can be seen in FIG. 2, the internal components of the intramedullary nail assembly 100 include a lag screw lock 150, an end cap 170, and a thread lock 190. The lag screw lock 150, the end cap 170, and the thread lock 190 are all positioned within the hollow upper portion 140 of the intramedullary shaft 102.

With reference now to FIGS. 3-6, the lag screw lock 150 includes a main body portion 152 and a threaded head portion 160 that is rotatably connected to the main body portion 152. The main body portion 152 is substantially cylindrical in shape and is designed and dimensioned to slide within the longitudinal channel 109 of the intramedullary shaft 102. The lag screw lock 150 includes a cross channel in the form of slot 154 that extends through the main body portion 154. The slot 154 is configured to receive the anti-rotation screw 114 such that the anti-rotation screw 114 may slide within the slot 154.

A protrusion 155 on the outer surface of the main body portion 152 of the lock 150 provides an alignment feature configured to engage a complimentary longitudinal groove 144 (see FIG. 3) formed in the upper portion 140 of the longitudinal channel 109 of the intramedullary shaft 102. This alignment feature 155 properly orients the lock 150 in the intramedullary shaft 102 and prevents the main body portion 152 of the lock 150 from rotating in the intramedullary shaft 102, while still allowing the main body portion 152 to slide within the channel 109. With the lock 150 properly oriented in the longitudinal channel 109 of the intramedullary shaft 102, the slot 154 of the lock 150 is aligned with the transverse channel 106 of the intramedullary shaft 102, such that the anti-rotation screw 114 may pass completely through the intramedullary shaft 102 via the transverse channel 106 of the intramedullary shaft 102 and the slot 154 of the lock 150.

Figure 5:
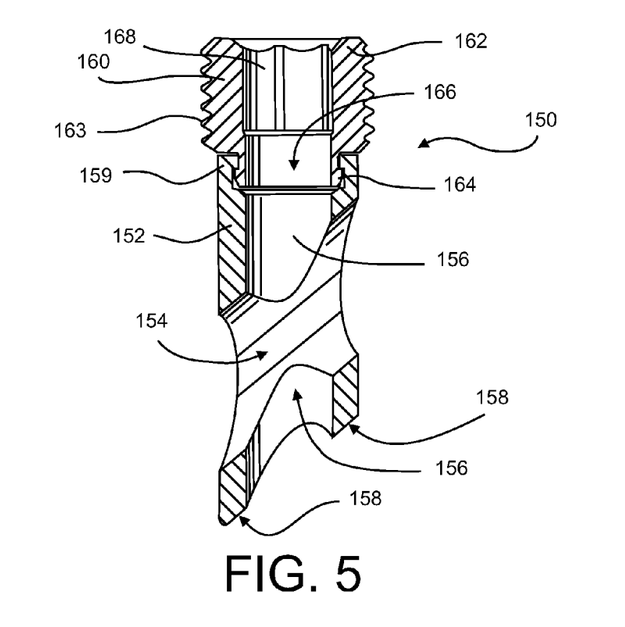
FIG. 5 shows a cutaway view of a locking key of the intramedullary nail assembly of FIG. 1.
Figure 6:
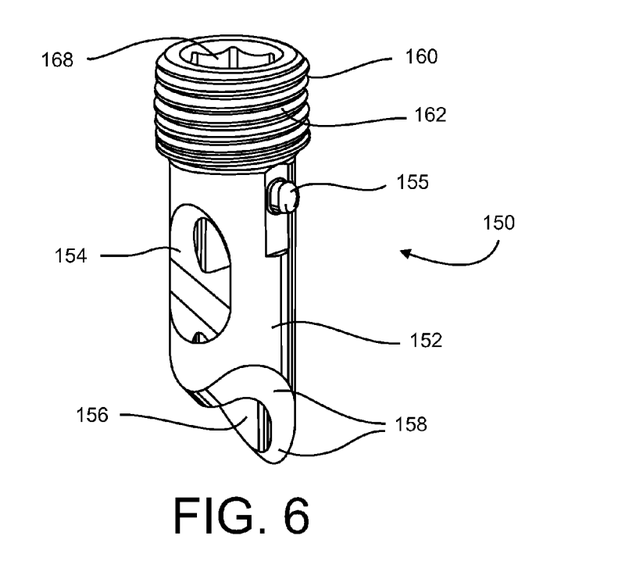
FIG. 6 shows a perspective view of the locking key of FIG. 5.

As best seen in FIG. 5, the main body portion 152 is hollow in a longitudinal direction such that a longitudinal passage 156 extends from the top to the bottom of the main body portion 152. Openings to the passage 156 are found at the top and bottom of the main body portion 152. At the bottom of the main body portion 152 a lower rim 158 is formed around the opening, with the rim 158 defining a locking surface configured to engage the lag screw 112. At the top of the main body portion 152 an opposing rim 159 defines a bearing surface that connects the head 160 to the main body portion 152 such that the head 160 is rotatable relative to the main body portion 152. In particular, the rim 159 includes an annular groove and a disc portion 164 of the head 160 fits in the annular groove to allow the head 160 to rotate relative to the main body portion 152.

The head portion 160 is generally cylindrical in shape and includes a threaded upper portion 162 connected to the lower disc portion 164. The head portion is hollow and includes an outer threaded surface. A longitudinal passage 166 in the head portion 160 leads to the longitudinal passage 156 in the main body portion 152, and thus provides a continuous longitudinal passage that extends completely through the lock 150. The continuous longitudinal passage results in a cannulated lock member 150 with a longitudinal passage that is coaxial or otherwise aligned with the longitudinal channel 109 of the intramedullary nail and facilitates passage of a ball nosed guide wire through the lock member 150 during implantation of the assembly 100 in a patient.

The outer surface of the threaded upper portion 162 of the head 160 includes threads 163 that engage complimentary threads 142 formed in the hollow upper portion 140 of the intramedullary shaft 102. The inner surface of the threaded upper portion 162 of the head 160 includes a drive surface 168 configured to receive a drive tool, such as a screw driver and impart rotational torque to the head portion 160. When the head portion 160 is rotated, the lock 150 moves in an axial direction along the longitudinal channel 109 of the intramedullary nail 102. When the lag screw lock 150 is driven down into the intramedullary shaft 102, the locking surface 158 on the main body portion 152 engages one of the grooves 134 on the lag screw 112 and prevents rotation of the lag screw 112. If the lock 150 is driven far enough, the lock will tightly clamp the lag screw in the transverse passage 104 to prevent sliding of the lag screw along its axis 103.

Figure 3:
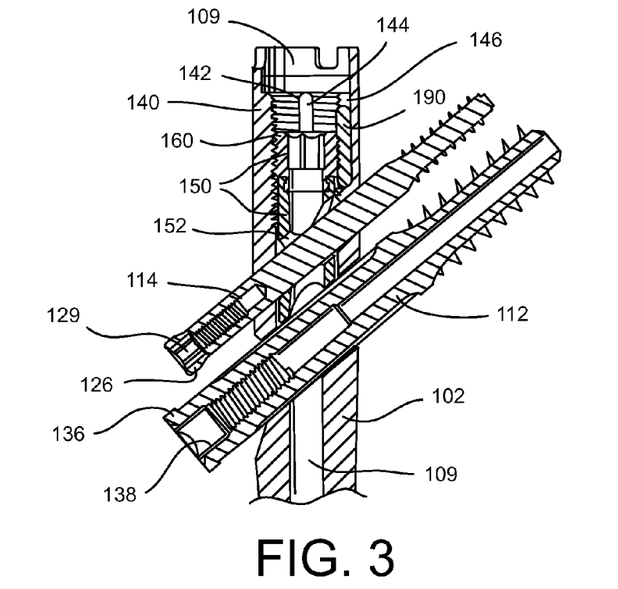
FIG. 3 is a partial cutaway view of the intramedullary nail assembly of FIG. 1 with a lag screw lock member positioned in the assembly.
Figure 4:
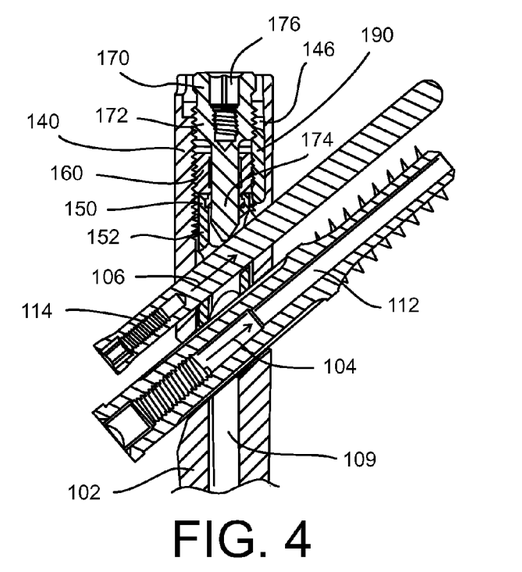
FIG. 4 is the partial cutaway view of the intramedullary nail assembly of FIG. 3 with an impinging end cap positioned in the assembly.

The thread lock 190 of the intramedullary nail assembly is shown in each of FIGS. 2-4. The thread lock 190 is provided as a relatively short rod comprised of a polymer material. The rod 190 is inserted in a longitudinal groove 146 that cuts across and into the threads 142 on the upper portion 140 of the intramedullary nail 102. The polymer material may be, for example, a low density polyethylene material exhibiting increased ductility. With the thread lock 190 positioned in the longitudinal groove, the threads 163 on the head portion 160 of the lag screw lock 150 cut into the surface of the rod 190 when the head portion 160 is driven in the intramedullary nail 102. The thread lock 190 provides increased friction against the threads 163 on the head portion and thus tends to lock the head portion in place in the intramedullary nail 102.

With particular reference to FIG. 4, the end cap 170 is also configured to engage the threads 142 on the upper portion 140 of the intramedullary nail 102. The end cap 170 in this embodiment is provided as an impinging in-cap that is positioned inside of the nail 102 within the longitudinal channel 109. The end cap 170 includes a threaded upper portion 172 and a lower post portion 174. The threaded upper portion 172 is substantially cylindrical in shape with a threaded outer surface. The threads on the outer surface of the upper portion 172 are configured to engage the complimentary threads 142 on the intramedullary nail 102. The inner surface 176 of the threaded upper portion 172 provides a drive surface for the end cap 170. A driving device, such as a screw driver, may be inserted into the end cap 170 to engage the inner surface 176 and provide a rotational torque to the end cap. When the end cap 170 is rotated the threaded upper portion 172 cooperates with the threads 142 on the intramedullary shaft to drive the end cap in a longitudinal direction within the intramedullary shaft. When the end cap 170 is driven down into the intramedullary nail 102, the lower post portion 174 of the end cap extends into the longitudinal passage 156 on the lag screw lock 150 and contacts the anti-rotation screw 114, as shown in FIG. 4. In particular, the post portion 174 engages one of the grooves 124 on the anti-rotation screw and prevents rotation of the anti-rotation screw 114. If the in cap 170 is driven far enough, the post portion 174 will tightly clamp the anti-rotation screw in the transverse passage 106 to prevent sliding of the anti-rotation screw along its axis 105. Furthermore, when the end cap 170 is driven far enough in the intramedullary nail 102, the threads on the end cap will engage the thread lock 190 and lock the end cap in place.

Figure 8:
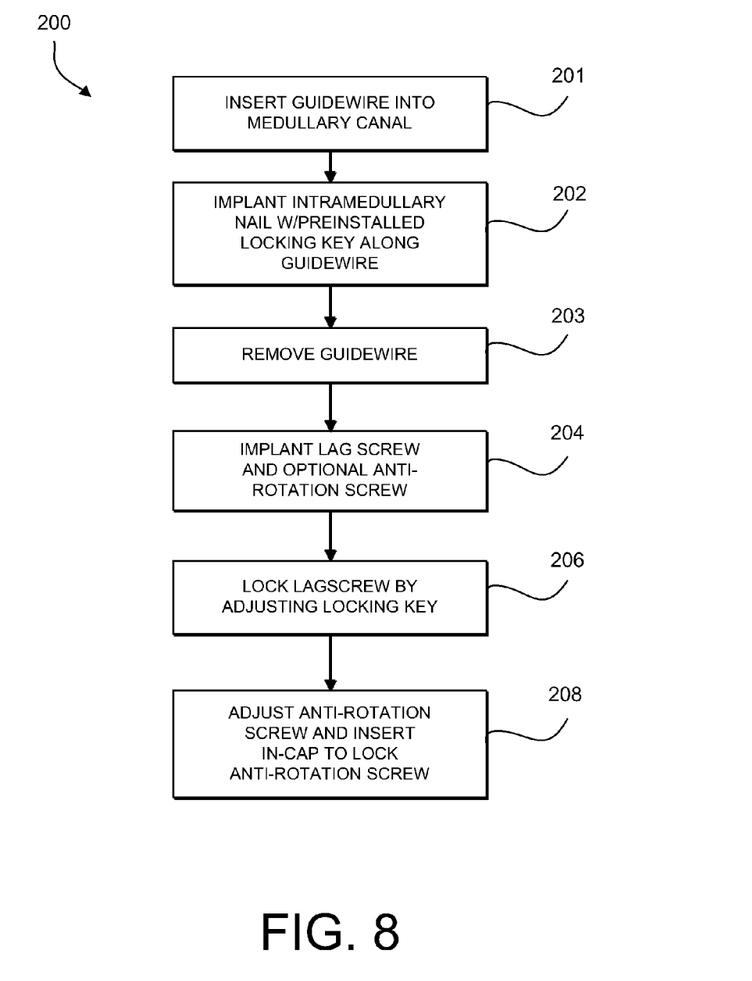
FIG. 8 is a flowchart of steps taken during a surgical procedure with the intramedullary nail assembly of FIG. 1.

Operation and implantation of the intramedullary nail assembly 100 is explained with reference to the flowchart 200 of FIG. 8. As shown in FIG. 8, the implantation process begins with step 201 when the surgeon inserts a ball nosed guidewire into the medullary canal of the fractured long bone. Then, in step 202, the intramedullary nail 102 is implanted in the medullary canal with the guidewire inserted through the longitudinal canal 109 of the nail 102. The lag screw lock 150 is preinstalled in the longitudinal canal 109 of the intramedullary nail 102 before the intramedullary nail is implanted. Thus, when the guidewire is inserted through the longitudinal canal 109, the guidewire also passes through the cannulated lock 150, and particularly through the longitudinal passage 156 of the main body and the longitudinal passage 166 on the head portion 160.

Once the intramedullary nail 102 is inserted in the medullary canal, the surgeon removes the ball nosed guidewire from the nail. Accordingly, the longitudinal passages in the nail 102 and cannulated lock 150 must all be of sufficient size to pass the ball at the end of the guidewire. For example, if the ball on the guidewire is ³⁄₁₆" in diameter, the diameter of the longitudinal passages 156 and 166 in the cannulated lock member 150 may be about ¼".

After removal of the ball nosed guidewire in step 203, the lag screw 112 is implanted in the patient in step 204, with the lag screw 112 passing through the first transverse passage 104 of the nail 102. If desired, the surgeon may also insert the anti-rotation screw 114 through the second transverse passage 106 of the nail. Because the lag screw lock 150 provides for passage of the anti-rotation screw, the surgeon may choose to implant the anti-rotation screw either before or after implantation of the lag screw. The surgeon locks the lag screw 112 in place in step 206 by rotating the head 160 of the lock. When the head of the lock is rotated, the main body 152 of the lock 150 moves in the longitudinal direction until the locking surface 158 contacts one of the grooves 134 of the lag screw.

The arrangement of the lag screw lock 150 allows the surgeon to adjust the position of the anti-rotation screw 114 even after the lag screw 112 is locked in place. In particular, the passage 154 through the main body of the lock 150 allows the anti-rotation screw to slide within the lock 150 and the nail 102. As noted in step 208, once the anti-rotation screw is properly positioned, the end cap 170 is inserted in the longitudinal channel 109 of the nail 102 and rotated. When the end cap 170 is rotated, the post 174 of the end cap engages one of the grooves 124 of the anti-rotation screw to lock the anti-rotation screw in place.

Although the intramedullary nail with locking key has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An intramedullary nail assembly comprising:
   an intramedullary shaft including a longitudinal channel, a first transverse passage and a second transverse passage, wherein the first transverse passage is configured to receive a lag screw and wherein the second transverse passage is configured to receive an anti-rotation shaft;
   a cannulated lag screw lock member positioned in the longitudinal channel of the intramedullary shaft, the lag screw lock member including a longitudinal passage and a locking surface, wherein the longitudinal passage extends through the lag screw lock member and is open to the longitudinal channel of the intramedullary shaft, and wherein the locking surface is configured to engage the lag screw and prohibit rotation of the lag screw in the first transverse passage; and
   a cap positioned in the longitudinal channel of the intramedullary shaft, the cap including a locking surface configured to engage the anti-rotation shaft and prohibit rotation of the anti-rotation shaft in the second transverse passage;
   wherein:
   the lag screw lock member includes a substantially cylindrical body portion rotatably connected to a threaded head portion, the cylindrical body portion and the threaded head portion defining the longitudinal passage;
   the cylindrical body portion includes the locking surface of the lag screw lock member and defines a cross slot aligned with the second transverse passage in the intramedullary shaft, the cross slot being configured to receive the anti-rotation shaft; and
   the threaded head portion engages complimentary threads in the longitudinal channel of the intramedullary shaft such that rotation of the threaded head portion results in movement of the cylindrical body portion along a longitudinal axis of the intramedullary shaft;
   wherein:
   the cap includes a threaded upper portion and a lower post portion, the lower post portion including the locking surface of the cap;
   the threaded upper portion of the cap engages the complimentary threads in the longitudinal channel of the intramedullary shaft;
   the lower post portion extends into the longitudinal passage to position the locking surface of the cap proximate the cross slot; and
   a thread lock,
   wherein:
   the longitudinal channel of the intramedullary shaft defines a longitudinal groove that cuts across and into the complimentary threads on an upper portion of the intramedullary nail, the thread lock being positioned in the longitudinal groove such that it engages both (1) the threaded head portion of the lag screw lock member and resists rotation of the threaded head portion relative to the complimentary threads, and (2) the threaded upper portion of the cap.

2. The assembly of claim 1, further comprising:
   a lag screw received in the first transverse channel.

3. The assembly of claim 2, wherein the lag screw includes a plurality of suture holes.

4. The assembly of claim 1, further comprising:
   an anti-rotation shaft received in the second transverse channel.

5. The assembly of claim 1, wherein the cap includes an uppermost portion opposite the locking surface, the uppermost portion at least partially disposed in the longitudinal channel of the intramedullary shaft.

\* \* \* \* \*